(12) United States Patent
Zhong

(10) Patent No.: US 9,566,391 B2
(45) Date of Patent: Feb. 14, 2017

(54) PROTECTIVE NEEDLE SHIELD

(76) Inventor: Bing-Tang Zhong, Houston, TX (US)

( * ) Notice: Subject to any disclaimer, the term of this patent is extended or adjusted under 35 U.S.C. 154(b) by 501 days.

(21) Appl. No.: 12/545,067

(22) Filed: Aug. 20, 2009

(65) Prior Publication Data

US 2011/0046564 A1 Feb. 24, 2011

(51) Int. Cl.
*A61M 5/32* (2006.01)
(52) U.S. Cl.
CPC .... *A61M 5/3216* (2013.01); *A61M 2005/3217* (2013.01)
(58) Field of Classification Search
CPC .................. A61M 2005/3217; A61M 5/3216
USPC ......................................... 604/192–198, 110
See application file for complete search history.

(56) References Cited

U.S. PATENT DOCUMENTS

| | | | | |
|---|---|---|---|---|
| 5,152,751 A * | 10/1992 | Kozlowski | ............. | 604/192 |
| 5,693,022 A * | 12/1997 | Haynes | ............. | 604/192 |
| 5,913,846 A * | 6/1999 | Szabo | ............. | 604/263 |
| 6,120,482 A * | 9/2000 | Szabo | ............. | 604/192 |
| 2006/0224122 A1* | 10/2006 | Bosel et al. | ............. | 604/192 |

* cited by examiner

*Primary Examiner* — Imani Hayman
(74) *Attorney, Agent, or Firm* — Nick A Nichols, Jr.

(57) ABSTRACT

A needle shield assembly for enclosing a needle cannula includes a needle cannula having a needle hub at a proximal end thereof and a sharp distal end. A needle shield adapter is mounted to the needle hub and a needle shield is connected to the adapter. The needle shield is moveable between a first position enclosing the needle cannula and a second position exposing the needle cannula for use.

13 Claims, 8 Drawing Sheets

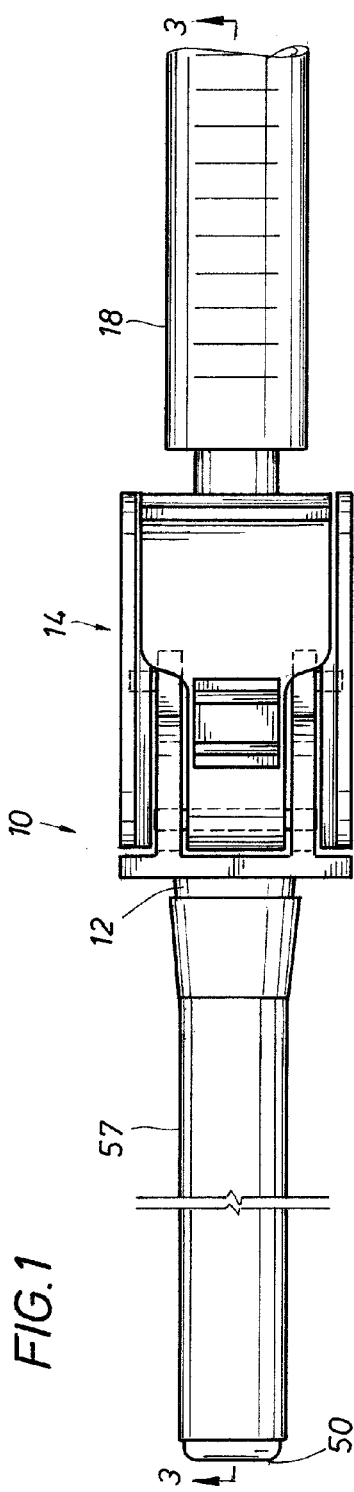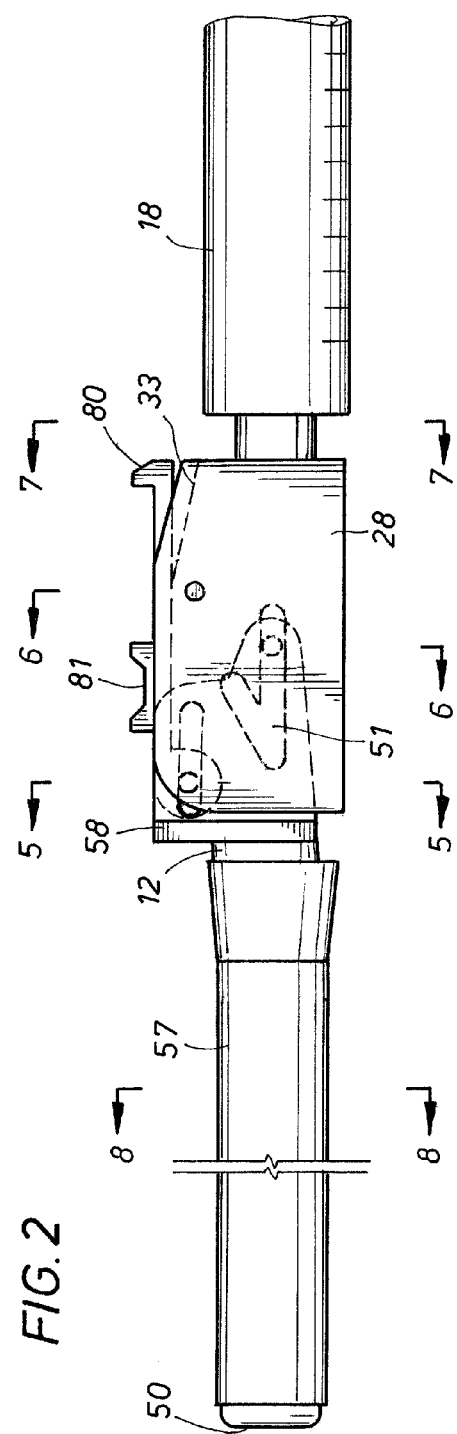

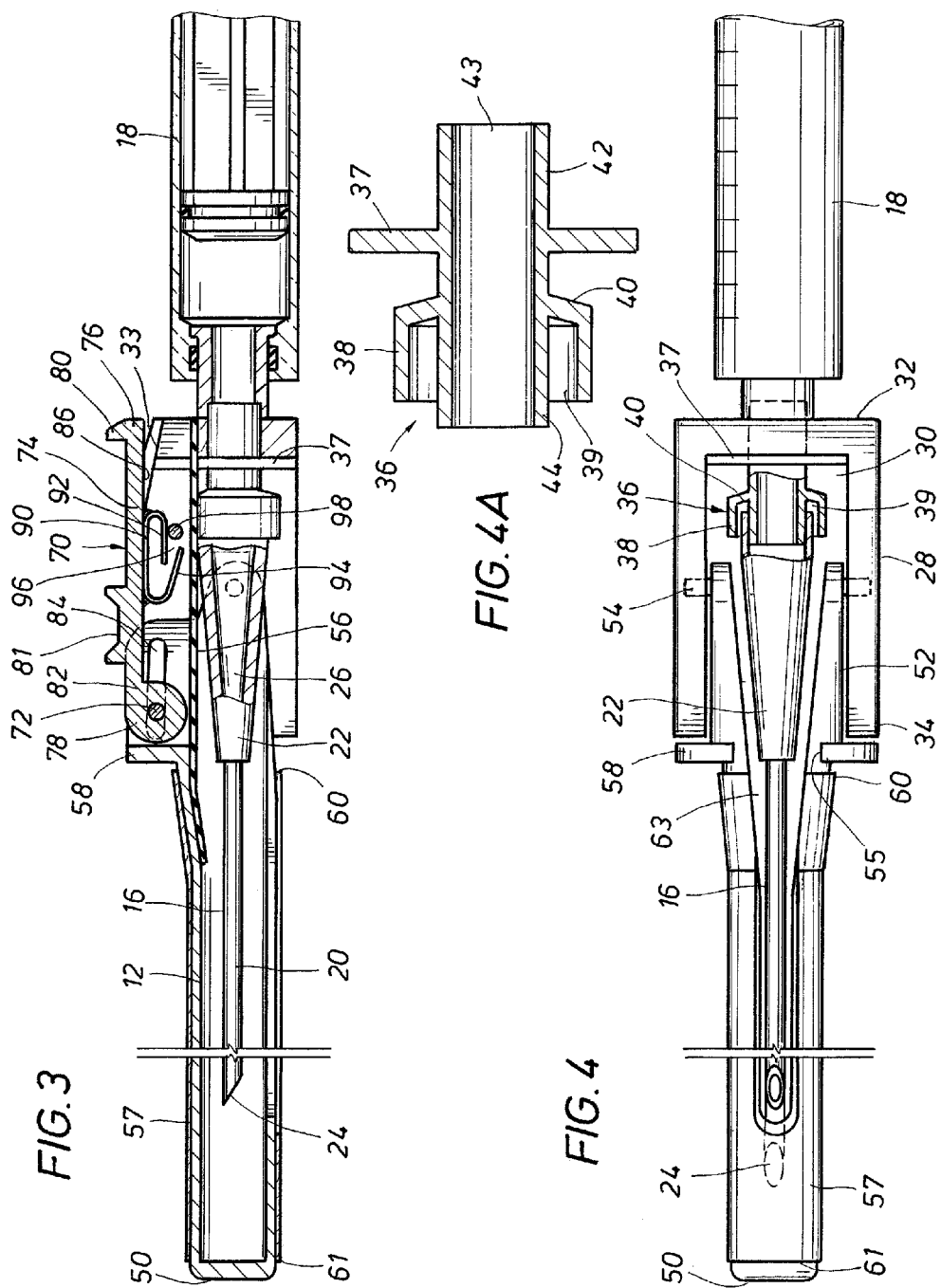

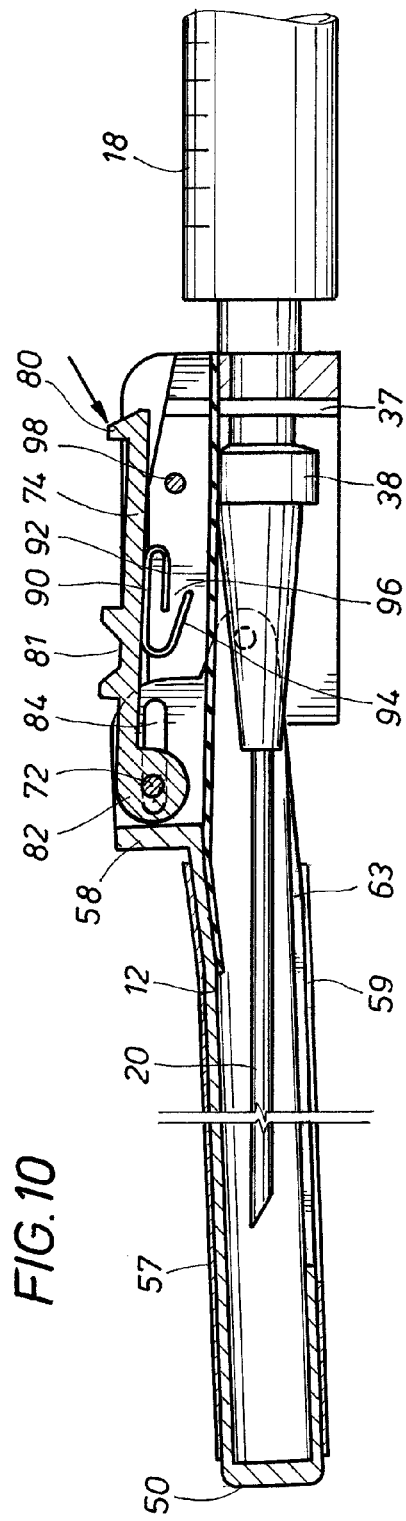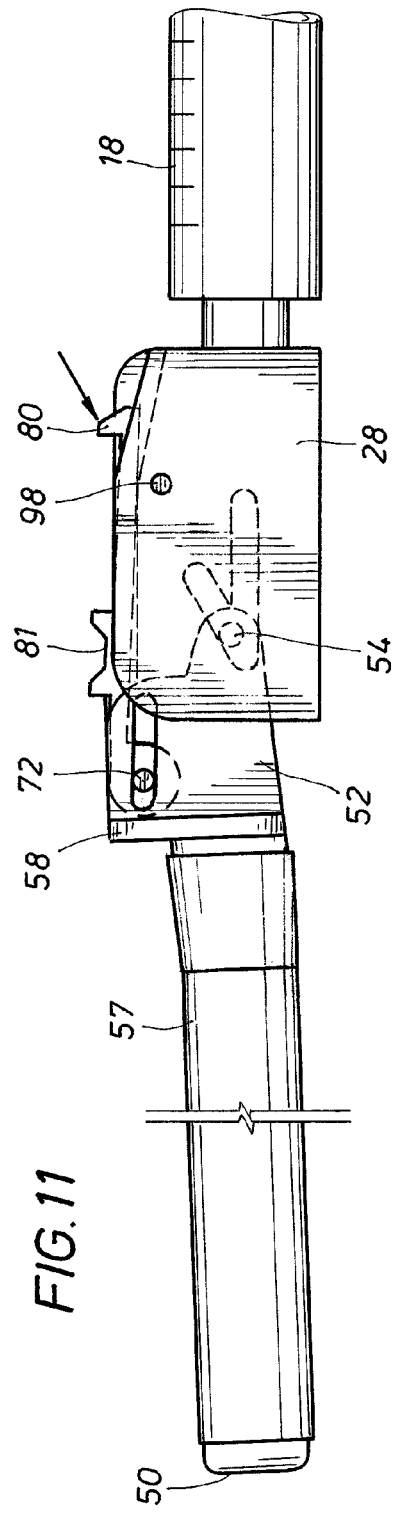

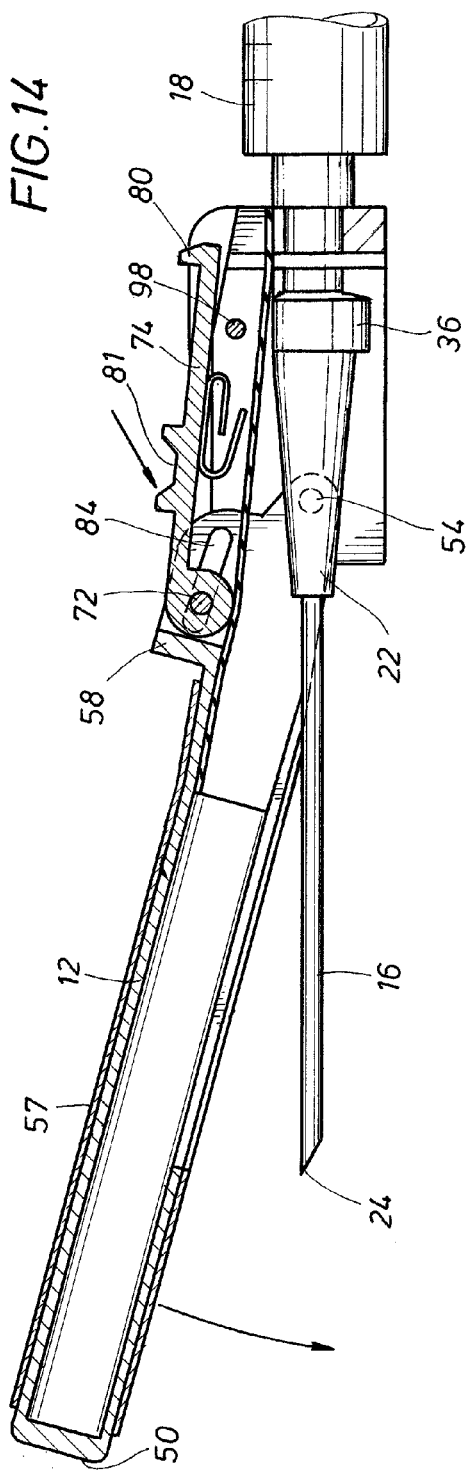

PROTECTIVE NEEDLE SHIELD

BACKGROUND OF THE INVENTION

The present invention relates to protective needle shields and more particularly to a device for preventing accidental needlesticks and contact with intramuscular or intravenous needles or the like used to inject and/or withdraw fluids from human and animal tissue.

Handling syringe needles, particularly intramuscular or intravenous needles, by medical personnel, technicians and others, can pose a serious risk. An accidental puncture or needlestick may result in transmission of fatal or chronic diseases, such as hepatitis B or AIDS. Exposure to body fluids by contacting the shaft of an intramuscular or intravenous needle after an injection also presents a serious danger of contamination.

SUMMARY OF THE INVENTION

A needle shield assembly in accordance with the present invention includes a needle cannula having a needle hub at a proximal end thereof and a sharp distal end. A needle shield adapter is mounted on the needle hub. A needle shield is pivotally connected to the adapter. The needle shield is moveable between a first (closed) position enclosing the needle cannula and a second (open) position exposing the needle cannula for use.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 1 a top plan view of a first embodiment of the present invention;

FIG. 2 is a side view of the invention shown in FIG. 1;

FIG. 3 is a section view of the invention shown in FIG. 2;

FIG. 4 is a partially broken away bottom view of the invention shown in FIG. 2;

FIG. 4A is a section view of a needle hub connector of the invention;

FIG. 10 is a section view of the needle shield of the invention demonstrating initial movement of the needle shield to an open position;

FIG. 11 is a side of the needle shield of the invention shown in FIG. 10;

FIG. 14 is a section view of the needle shield of the invention demonstrating movement of the needle shield to the closed position;

FIG. 15 is a side view of the needle shield of the invention demonstrating movement of the needle shield to the closed position;

DETAILED DESCRIPTION OF A PREFERRED EMBODIMENT

Figure 5:
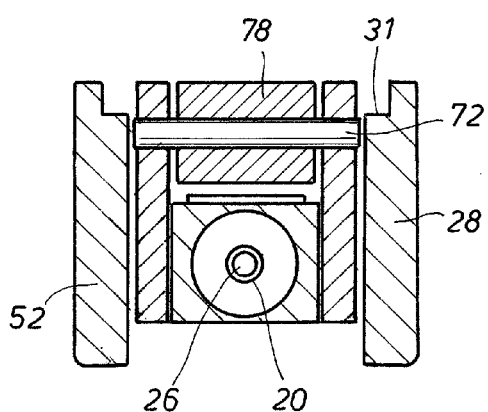
FIG. 5 is a section view of the invention taken along line 5-5 of FIG. 2.
Figure 6:
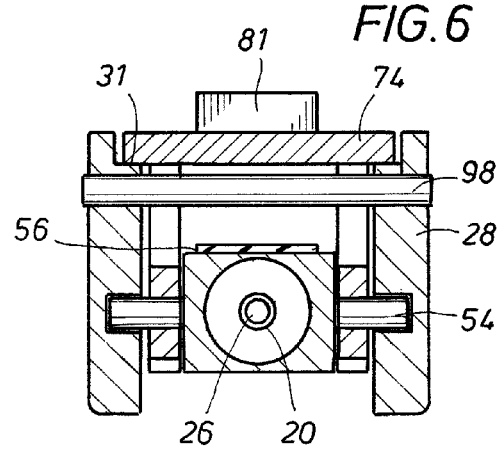
FIG. 6 is a section view of the invention taken along line 6-6 of FIG. 2.
Figure 7:
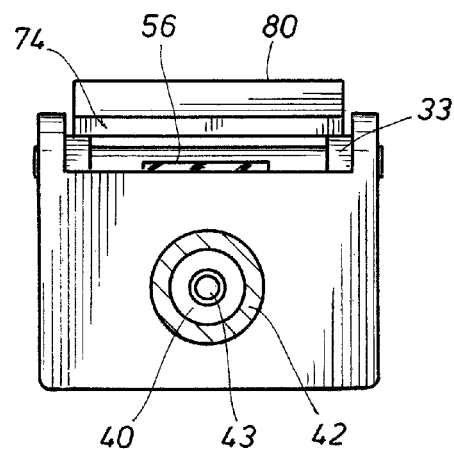
FIG. 7 is a section view of the invention taken along line 7-7 of FIG. 2.
Figure 8:
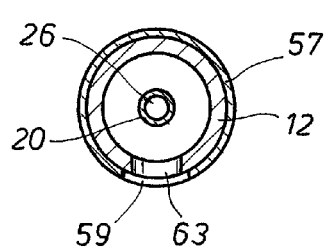
FIG. 8 is a section view of the invention taken along line 8-8 of FIG. 2.
Figure 9:
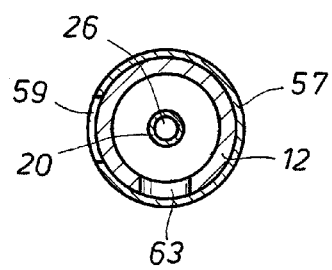
FIG. 9 is a section view of the invention taken along line 9-9 of FIG. 17.

Referring first to FIGS. 1-4, a first embodiment of the needle shield assembly of the invention is generally identified by the reference numeral 10. Needle shield assembly 10 includes a needle shield 12 and an adapter assembly 14. The needle shield assembly 10 may be used with a conventional needle 16 and a syringe 18 or similar device. Referring now specifically to FIGS. 3 and 4, the needle 16 comprises a needle cannula 20 fixed to a needle hub 22 at one end thereof. The opposite or distal end of the cannula 20 terminates in a sharp tip 24. A lumen 26 extends through the needle 16 for permitting fluid flow therethrough.

Use and disposal of conventional syringe needles pose a risk of needlestick injuries to health care workers, particularly, when disposing of or recapping used needles, administering parenteral medications, drawing blood, and collecting linens and trash that may be bundled with discarded needles. Currently, needles are removed from their protective packaging prior to use and connected to a syringe in a conventional manner and a cover cap is removed to expose the needle cannula. After use, the needle cannula is recapped and the used needle is discarded. Two hands are required to recap the used needle, one to hold the syringe and the other to guide the needle cap over the needle cannula and secure it to the needle hub. Needlesticks while recapping a needle commonly occur and expose the health care worker to injury and risk of exposure to bacterial and viral infections and other diseases that may be fatal.

Referring still to FIGS. 3 and 4, the adapter assembly 14 includes sidewalls 28 and a connecting rear wall 30. The sidewalls 28 and rear wall 30 form an elongate substantially U-shaped adapter housing. The sidewalls 28 are spaced apart and secured along respective longitudinal edges of the rear wall 30 and oriented substantially perpendicular to the rear wall 30. The adapter housing includes a proximal end 32 and a distal end 34, both of which are open and define the length of the adapter housing. The upper longitudinal portion of the sidewalls 28 is cut back to form a shoulder 31 extending the length of the sidewalls 28. The shoulder 31 is substantially perpendicular to the sidewalls 28 and further includes a portion 33 that slopes downwardly near the proximal ends of the sidewalls 28.

A needle hub connector 36 is mounted between the sidewalls 28 proximate the proximal end 32 of the adapter housing. The connector 36 includes an upper portion 38 defining a generally frustoconically shaped cavity 39. The connector 36 is secured transverse to the longitudinal axis of the adapter housing by a circumferential flange 37 or the like extending outward from the connector 36. The connector 36 further includes a passageway 43 therethrough. The bottom or proximal end of the upper portion 38 is formed by a circumferential inwardly tapering shoulder 40 that terminates at the passageway 43. A hub connector extension member 42 extends downwardly from the shoulder 40. The extension member 42 may be adapted to fit to the connector end of the syringe 18 by friction or standard luer lock in a conventional manner. A tube 44 coaxially located within the cavity 39 and in axial alignment with the extension member 42 extends outwardly from the cavity 39. The extension member 42 and tube 44 form part of the passageway 43.

Referring still to FIGS. 3 and 4, the needle shield 12 is preferably an elongate cylindrical structure closed at a distal end 50. The lower or proximal end of the shield 12 is open and defined by extension members 52 that are spaced apart and parallel. Each extension member 52 includes a hinge pin 54 in the lower portions thereof. The pins 54 project outwardly from the extension members 52. The free ends of the pins 54 are received in grooves 51 formed in the sidewalls 28 of the adapter housing so that the needle shield 12 may pivot with respect to the needle 16 on an axis extending transversely through the sidewalls 28 of the adapter housing.

A longitudinal slot 63 forming and elongate side opening in the needle shield 12 extends from the open proximal end of the needle shield 12 to a point below the distal end 50 thereof. The lower end of the slot 63 is defined by the needle shield extension members 52 and is sufficiently sized to accommodate a conventional injection needle and its sheath to pass therethrough and connect to the needle hub connector 36. The upper end of the slot 63 terminates at a point below the closed distal end 50 of the needle shield 12 so that the tip or upper portion of the needle shield 12 defines a partially enclosed cavity 53. When the needle shield 12 is in the first or closed position, the tip 24 of the needle 16 extends into the needle shield cavity 53 preventing pivoting of the needle shield 12 and exposing the needle 16.

The needle shield 12 further includes a circumferential shoulder 58 that extends partially about the proximal end of the needle shield 12. The shoulder 58 defines the transition point where the proximal end of the needle shield 12 bifurcates to form the extension members 52. The opposed ends 55 of the shoulder 58 terminate at the proximal end of the slot 63 formed in the needle shield 12.

The needle shield 12 is connected to the hub connector 36 by an elastic tendon 56, such as a high quality rubber band, having one end secured to the inner surface of the needle shield 12 and an opposite end thereof secured to the outer surface of the upper portion 38 of the hub connector 36. The tendon 56 is under tension so that it applies a downward pulling force on the needle shield 12. Downward movement of the needle shield 12 is limited by engagement of the circumferential shoulder 58 with the distal end 34 of the adapter housing.

The needle shield assembly 10 further includes a sheath or sleeve 57 over the needle shield 12. The sleeve 57 comprises a hollow cylindrical body open at both ends thereof. A longitudinal slot 59 extends from a lower end 60 to a position near the upper end 61 of the sleeve 57. The length of the slot 59 is substantially equal to the length of the slot 63 in the needle shield 12. The sleeve 57 includes a circumferential internal lip proximate the upper end 61 thereof. The circumferential lip is sized and configured for engagement with a circumferential groove formed in the needle shield 12 proximate the distal end 50 thereof. The sleeve 57 slides over the needle shield 12 substantially the full length of the needle shield 12. Engagement of the internal circumferential lip with the circumferential groove prevents axial separation between the sleeve 57 and the needle shield 12 while permitting the sleeve 57 to rotate about the needle shield 12. In the closed position, shown in FIG. 1, the sleeve 57 covers the slot 63 of the needle shield 12 to maintain the needle 16 in a sterile and protected condition within the needle shield 12. When the needle 16 is to be used, the sleeve 57 is rotated so that the slot 59 is positioned in the same orientation as the slot 63 of the needle shield 12, shown in FIG. 4, permitting pivoting of the needle shield 12 away from the needle cannula 20 to an open or second position and exposing the needle 16.

A shield actuator 70 is pivotally connected to the proximal end of the needle shield 12 by a pivot pin 72. The actuator 70 comprises a rigid planar body 74 having opposed proximal and distal ends 76 and 78, respectively. The proximal end 76 defines an actuator knob 80 configured for receiving digitally directed forces thereon. A second actuator knob 81 is provided proximate the distal end 78 of the actuator 70. The distal end 78 further defines a pivot arm 82 having an aperture extending therethrough for receiving the pivot pin 72 therein. The pivot arm 82 is sized and configured so that it may be disposed between the extension members 52 at the proximal end of the shield 12. The opposed ends of the pivot pin 72 are received in grooves 84 formed in the extension members 52 in such a manner that the shield actuator 70 may move axially relative to the shield 12 and pivot about the pivot pin 72.

A lock mechanism is mounted on the bottom surface 86 of the actuator body 74. The lock mechanism comprises an elongate metal body having a central portion 90 fixedly secured to the bottom surface 86 of the actuator body 74. An end portion 92 is bent toward the central portion 90 but spaced therefrom and oriented substantially parallel thereto. The opposite end portion 94 is likewise bent toward the central portion 90 and extends beyond the end portion 92 defining a gap 96 therebetween. A lock pin 98 extends transversely between the sidewalls 28 of the adapter housing and secured thereto. The lock pin 98 is positioned below the lock mechanism. In the initial unlocked position shown in FIG. 3, the end portion 94 extends past the lock pin 98 so that the lock pin 98 is positioned in the gap 96 thereby retaining the actuator body 74 in the unlocked position shown in FIG. 3. After the needle 16 has been used, the needle shield is pivoted to the locked position shown in FIG. 16. A downward force applied to the actuator body 74 forces the lock mechanism against the lock pin 98 so that the lock pin 98 is captured in the space between the end portion 92 and the central portion 90 of the lock mechanism to the locked position shown in FIG. 16.

Figure 12:
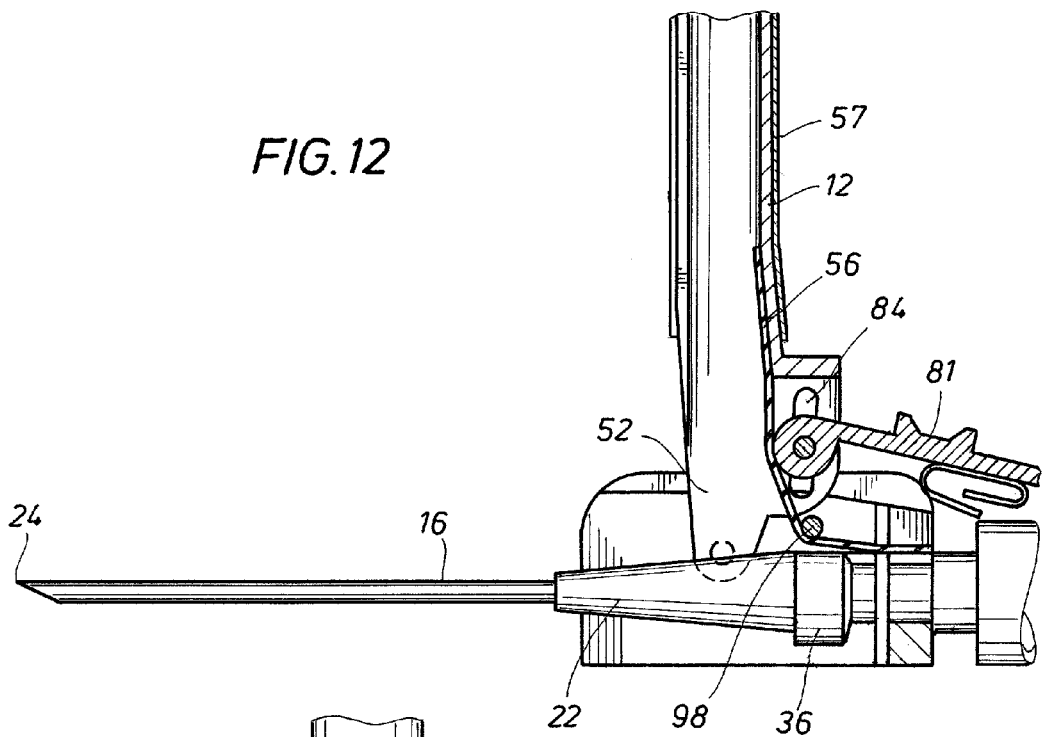
FIG. 12 is a partially broken away section view of the needle shield of the invention in the open position.
Figure 13:
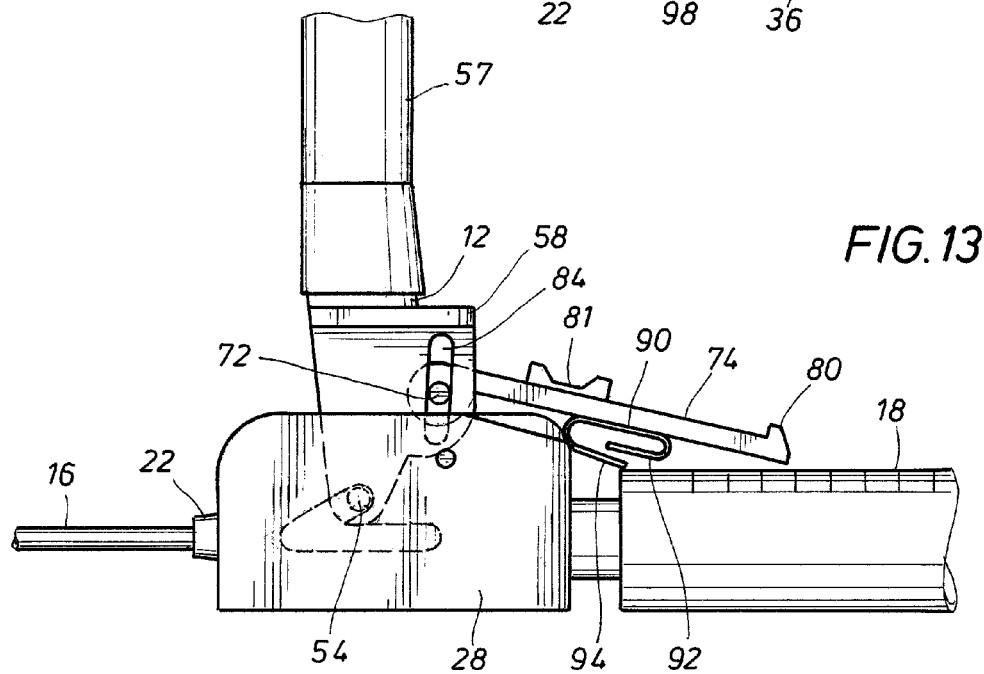
FIG. 13 is a partially broken away side view of the needle shield of the invention in the open position.

Referring now to FIGS. 10-17, the sequence of opening, closing and locking the needle shield of the invention is illustrated. To avoid discarding conventional injection needles, the needle shield assembly 10 is designed for use with available conventional injection needles. First, a convention injection needle 16 is secured to the needle hub connector 36 and is enclosed within the needle shield 12 as shown in FIGS. 10 and 11. The slot 59 of the sleeve 57 is aligned with the slot 63 of the needle shield 12 and digital force, such as may be exerted by the thumb or finger of a medical technician, is applied to the actuator knob 80 such that the needle shield 12 moves upward relative to the needle 16 until the pins 54 of the needle shield extensions 52 reach the top of the linear or straight leg of the J-shaped groove 51 formed in the sidewalls 28 of the adapter housing. At this point, the sharp tip 24 of the needle 16 is exposed and may pass through the slot 63 of the needle shield 12. While the actuator knob 80 is pressed against the sloped portion 33 of the sidewalls 28, the pins 54 move into the angular leg of the J-shaped groove 51 upon release of the actuator knob 80 causing the needle shield 12 to rotate away from the needle 16 under the pulling force of the elastic tendon 56 to an open position and expose the needle 16 as shown in FIGS. 12 and 13. The syringe 18 and needle 16 may then be used in a conventional manner to administer a drug or the like.

Figure 16:
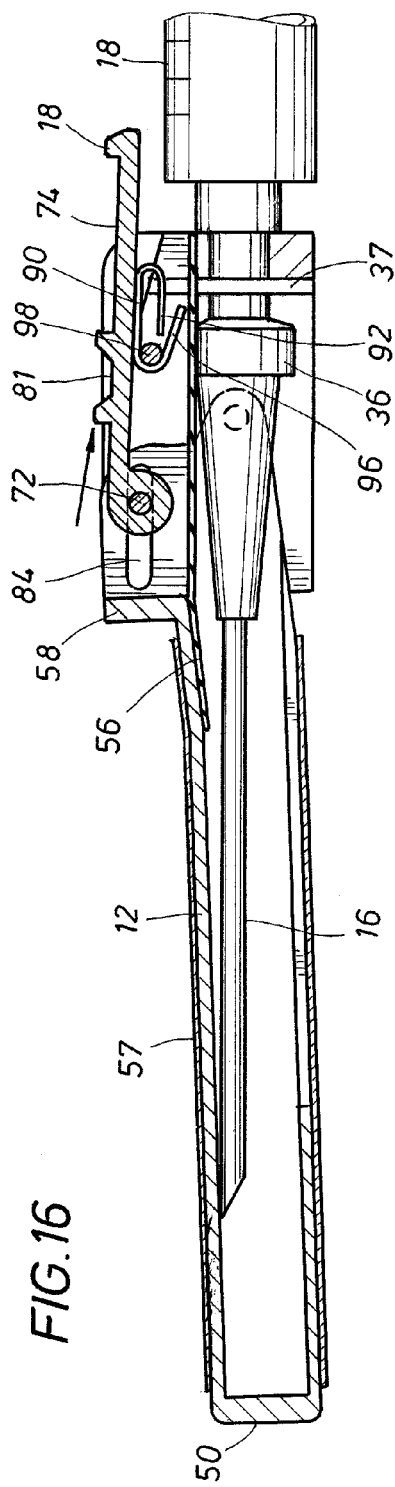
FIG. 16 is a side view of the needle shield of the invention in the locked position.
Figure 17:
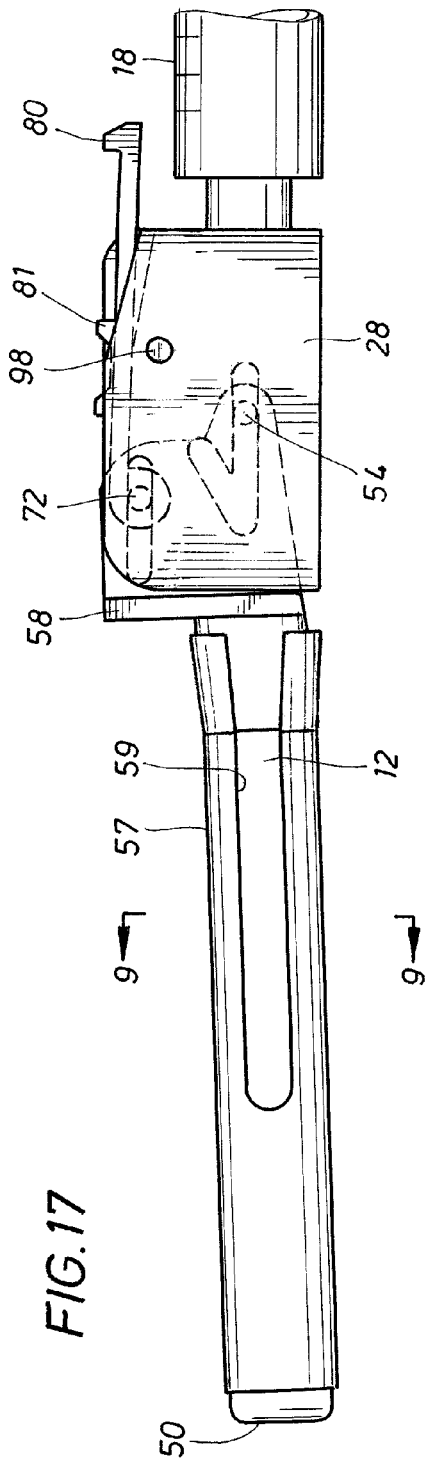
FIG. 17 is a side view of the needle shield of the invention in the locked position.

After use, the medical technician applies a digital force to the actuator knob 81 such that the needle shield 12 pivots in the direction shown in FIGS. 14 and 15 to substantially enclose or encase the needle 16 as shown in FIGS. 16 and 17. Downward force is then applied to the knob 81 so that the ends 92 and 94 of the locking mechanism advance past the lock pin 98 in locking engagement therewith as shown in FIGS. 16 and 17. Once locked, the needle shield 12 may not be actuated again to expose the needle 16 without destroying the lock mechanism and the needle hub housing. The medical technician may open, close and lock the needle shield of the present invention with a single digit, such as the thumb, and thereby eliminate the possibility of needlesticks. The needle shield of the present invention is also particularly useful in situations where an injection needle must be repeatedly used during a surgical procedure. For example, during surgery an anesthetist uses the same needle and syringe to administer medicine to the patient through infusion lines. In such a situation, the present invention may be used as described above but the needle shield is not locked until after the final use of the injection needle. Between injections, the needle shield is rotated to the closed position to protect the injection needle between uses and prevent needlesticks. The digits of the medical technician do not extend beyond the adapter housing when applying digital force to open and close the needle shield 12 and therefore cannot come into contact with the needle tip 24.

Figure 18:
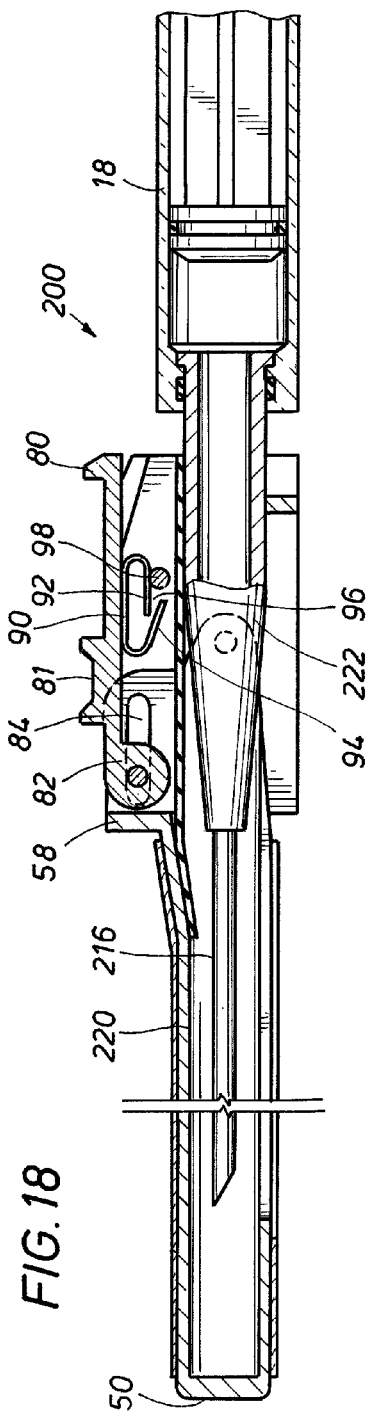
FIG. 18 is a section view of a second embodiment of the present invention.
Figure 19:
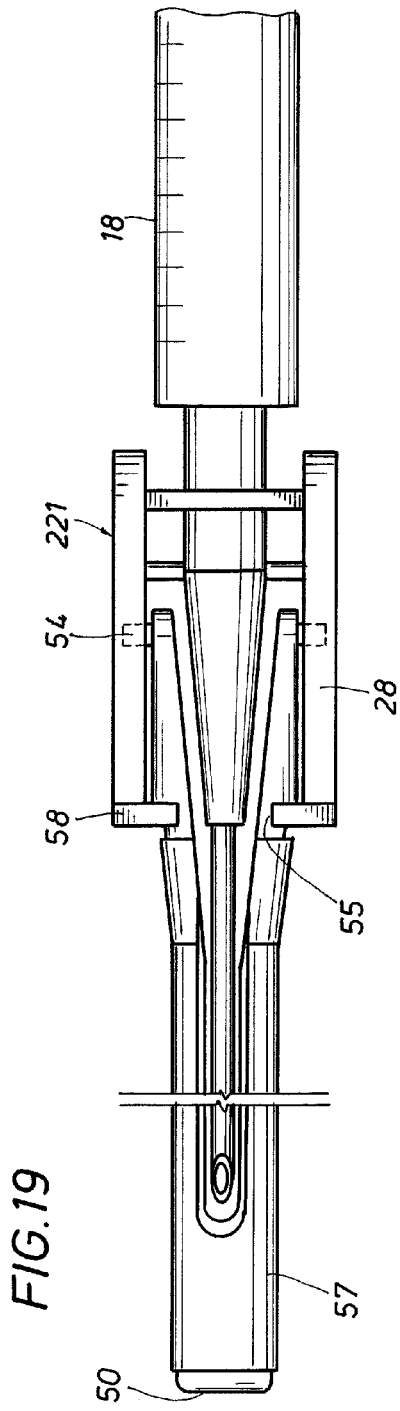
FIG. 19 is a partially broken away bottom view of the invention shown in FIG. 18.

Referring now to FIGS. 18 and 19, a second embodiment of the invention is generally identified by the reference numeral 200. The needle shield assembly 200 is substantially the same as the needle shield assembly 10 described above with the exception that the needle hub connector 36 of the first embodiment described above is eliminated. The U-shaped adapter housing 221 illustrated in FIGS. 18 and 19 is mounted directly on the needle hub 222 so that the needle shield 220 and needle 216 define a unitary needle assembly that may be used with a syringe 18 in a conventional manner. The needle shield assembly 200 shown in FIGS. 18 and 19 illustrates a unique needle shield design to replace the conventional injection needle assembly that requires two hands to use, upon depletion of the currently available supply of the conventional needle assembly.

While a preferred embodiment of the invention has been shown and described, other and further embodiments of the invention may be devised without departing from the basic scope thereof, and the scope thereof is determined by the claims which follow.

The invention claimed is:

1. A needle shield assembly, comprising:
   a) a needle cannula, wherein said needle cannula includes a needle hub secured at a proximal end thereof and a sharp end at an opposite distal end thereof;
   b) an adapter assembly removeably securing said needle cannula to a syringe, said adapter assembly including an adapter housing and a needle hub connector mounted within said adapter housing;
   c) said adapter assembly further including a needle shield moveably connected to said adapter housing and rotatable between a first position wherein said needle cannula is enclosed by said needle shield and a second position wherein said needle cannula is exposed for use; and
   d) a tendon member having a distal end secured to said needle shield and a proximal end secured to said needle hub connector.

2. The needle shield assembly of claim 1 wherein said adapter housing includes first and second spaced apart sidewalls and a connecting wall extending between said sidewalls, said sidewalls including J-shaped grooves formed in opposed facing surfaces thereof.

3. The needle shield assembly of claim 2 including a shield actuator pivotally connected to a proximal end of said needle shield disposed for rotating said needle shield between said first and second positions, said shield actuator including a proximal end and a distal end.

4. The needle shield assembly of claim 3 wherein said shield actuator includes a first actuator knob defining said distal end of said shield actuator and a second actuator knob located proximate the proximal end of said shield actuator.

5. The needle shield assembly of claim 4 wherein manipulation of said first actuator knob rotates said needle shield from said first position to said second position.

6. The needle shield assembly of claim 3 wherein said needle shield includes spaced apart extension members at the proximal end thereof, said extension members including elongate slots for slidably receiving a pivot pin extending through said shield actuator proximate the proximal end thereof.

7. The needle shield assembly of claim 3 wherein said needle shield includes spaced apart extension members defining the proximal end thereof and wherein each of said extension members include outwardly projecting pivot pins slidably received in said slots of said sidewalls.

8. The needle shield assembly of claim 3 wherein said shield actuator includes a locking means for locking said needle shield about said needle cannula.

9. The needle shield assembly of claim 2 wherein said adapter assembly includes the needle hub connector transversely mounted proximate the proximal end of said adapter housing.

10. The needle shield assembly of claim 9 wherein said needle hub connector includes a distal end for removably connecting said needle cannula to said needle hub connector, and further including a proximal end for removably attaching said needle cannula to the syringe.

11. The needle shield assembly of claim 1 wherein said needle shield includes an elongate side opening configured to permit said needle cannula to pass therethrough.

12. The needle shield assembly of claim 1 wherein said tendon member comprises an elastic tendon.

13. The needle shield assembly of claim 1 including a removable sleeve mounted about said needle shield, wherein said needle shield includes a circumferential detent for locking said sleeve thereon.

* * * * *